(12) United States Patent
Ohtsuki et al.

(10) Patent No.: US 6,197,758 B1
(45) Date of Patent: Mar. 6, 2001

(54) METHODS FOR SUPPLYING POSTGASTRECTOMIC MINERAL AND METHODS FOR TREATING POSTGASTRECTOMIC SYNDROME

(75) Inventors: Masako Ohtsuki; Atsutane Ohta; Toshio Takizawa; Takashi Adachi, all of Sakado (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 09/284,085

(22) PCT Filed: Oct. 8, 1997

(86) PCT No.: PCT/JP97/03597

§ 371 Date: Apr. 7, 1999

§ 102(e) Date: Apr. 7, 1999

(87) PCT Pub. No.: WO98/15196

PCT Pub. Date: Apr. 16, 1998

(30) Foreign Application Priority Data

Oct. 8, 1996 (JP) .................................................... 8-267096

(51) Int. Cl.[7] ..................... A61K 31/715; A61K 31/045; A61K 33/42; A61K 33/26; A61K 33/06
(52) U.S. Cl. ........................... 514/54; 514/724; 424/602; 424/646; 424/682
(58) Field of Search ..................... 514/54, 724; 424/602, 424/646, 682

(56) References Cited

U.S. PATENT DOCUMENTS 3,794,722 * 2/1974 Taya .................................... 424/147
5,434,061 * 7/1995 Ishiguro et al. ..................... 435/100
5,439,882 * 8/1995 Feola et al. .............................. 514/6
5,900,255 * 5/1999 Ohta et al. ........................... 424/602

FOREIGN PATENT DOCUMENTS

| 57-156419 | 9/1982 | (JP) . |
| 59-199626 | 11/1984 | (JP) . |
| 5-000067 | 1/1993 | (JP) . |
| 6-116154 | 4/1994 | (JP) . |
| 7-069902 | 3/1995 | (JP) . |
| 7-145064 | 6/1995 | (JP) . |
| 7-252156 | 10/1995 | (JP) . |
| 8-157379 | 6/1996 | (JP) . |

OTHER PUBLICATIONS

T. Ebata et al., "Nutritional Control Before and After Gastric Cancer Operation", (in Japanese), Cancer & Chemotherapy, 15, (1988), pp. 820–826.

* cited by examiner

*Primary Examiner*—Kevin E. Weddington
(74) *Attorney, Agent, or Firm*—Wenderoth, Lind & Ponack, L.L.P.

(57) ABSTRACT

An objective of the present invention is to provide compositions for supplying minerals to patients who underwent gastrectomy to thereby treat or prevent postgastrectomic syndrome. The composition for postgastrectomic mineral supply according to the present invention comprises an indigestible oligosaccharide and/or an indigestible sugar alcohol and a mineral.

14 Claims, 6 Drawing Sheets

METHODS FOR SUPPLYING POSTGASTRECTOMIC MINERAL AND METHODS FOR TREATING POSTGASTRECTOMIC SYNDROME

This application is a 371 of PCT/JP97/03597 filed Oct. 8, 1997.

BACKGROUND OF THE INVENTION

1. Field of Invention

The present invention relates to postgastrectomic mineral supplements and, more specifically, to therapeutic agents for postgastrectomic syndrome. The present invention also relates to methods for supplying Postgastrectomic mineral and methods for treating Postgastrectomic Syndrome.

2. Description of the Related Art

Gastric ulcers and stomach cancers that are caused by such factors as stresses arising from a complex modern society are typical adult diseases. Gastrectomy is performed for treating a variety of gastric diseases, most frequently, for treating stomach cancers and gastric ulcers.

Various mechanical or metabolic disorders occur after gastrectomy. For example, disorders such as postoperative hemorrhage, satural failure, and postoperative pancreatitis occur immediately or in the early stage after gastrectomy, while dumping syndrome, diarrhea, bone metabolism disorders and anemia are major disorders which occur after a certain period of time.

Bone metabolic disorders are mainly caused by malabsorption of calcium or vitamin D. Specifically, it is thought that bone metabolic disorders are caused by an insufficient uptake of calcium due to a reduction in the amount of diets and reduced solubility of calcium as a result of the reduced secretion of gastric acid due to the gastrectomy as well as a decrease thereby in calcium absorption. Moreover, diarrhea, dumping syndrome and the like are thought to interfere with the absorption of vitamin D that is essential for calcium absorption from the intestinal tract, triggering the resorption of calcium from the bones to the blood and the gradual development of bone lesions.

The reduced secretion of gastric hydrochloric acid as a result of gastrectomy also interferes with the absorption of iron which triggers a depletion of iron stored in the body to conceivably cause a form of anemia known as iron deficiency anemia. Further, after total gastrectomy, the lack of secretion of intrinsic factors such as transcobalamin from the gastric membrane will interfere with the absorption of vitamin B12, even if vitamin B12 is contained in sufficient quantities in ingested foods. This decreases stores of vitamin B12 in the liver to cause agastric pernicious anemia.

Thus, it was known that it is necessary to conduct adequate therapeutic management and alimentary therapy for a certain period after gastrectomy. For example, patients with bone metabolic disorders are fed diets rich in calcium, optionally, vitamin D or calcitonin formulations in combination. Anemia patients are fed diets rich in iron, optionally, iron formulations or vitamin B12. However, no effective postgastrectomic mineral supply has been reported and the management of postgastrectomic care may would be improved.

Meanwhile, indigestible oligosaccharides (particularly fructo-oligosaccharides) were reported to promote mineral absorption in healthy humans (Japanese Patent Laid-open No. 145064/1995 and Japanese Patent Laid-open No. 252156/1995).

SUMMARY OF THE INVENTION

The present inventors have now found that indigestible oligosaccharides and indigestible sugar alcohols extremely promote absorption of minerals (particularly, calcium and iron) in patients who underwent gastrectomy. Compared with healthy humans, patients who underwent gastrectomy have absorption disorders or are apt to have absorption disorders in the gastrointestinal tract. It was surprising to the inventors that indigestible oligosaccharides and indigestible sugar alcohols promote mineral absorption in patients who underwent gastrectomy.

Thus, the objective of the present invention is to provide a composition and method which effectively supplies minerals such as calcium and iron to patients who underwent gastrectomy.

Another objective of the present invention is to provide a composition and method for the treatment of postgastrectomic syndrome.

The composition for postgastrectomic mineral supply and the composition for the treatment of postgastrectomic syndrome according to the present invention comprise an indigestible oligosaccharide and/or an indigestible sugar alcohol and a mineral.

DESCRIPTION OF THE PREFERRED EMBODIMENTS

The expression "indigestible oligosaccharides" as used herein refers to oligosaccharides that are not at all or hardly digestible by digestive enzymes in the body.

In the present invention, the number of sugar residues of the oligosaccharides can be from 2 to 6. Monosaccharides comprising the oligosaccharides can be glucose, galactose, xylose, fructose, or combinations thereof.

Examples of indigestible oligosaccharides include fructo-oligosaccharides, raffinose, stachyose, galacto-oligosaccharides, xylo-oligosaccharides, and lactosucrose, preferable, fructo-oligosaccharides. The fructo-oligosaccharides have excellent physiological effects such as promotion of growth of bifidobacteria in the intestine, control of intestinal function, and prevention of dental caries.

Fructo-oligosaccharides as used herein refer to saccharides in which 1 to 3 fructose molecules are bound to the fructose moiety of sucrose through β1, 2 linkages, and mixtures thereof. Examples of fructo-oligosaccharides include 1-kestose, nistose, fructosylnistose, and mixtures thereof.

Raffinose as used herein refers to a trisaccharide Galα1→6Glcα1→2βFru, stachyose as used herein refers to a tetrasaccharide Galα1→6Galα1→6Glcα1→2βFru, and lactosucrose as used herein refers to a trisaccharide in which fructose is bound to the glucose moiety of lactose through β1, 2 linkage.

Galacto-oligosaccharides as used herein refers to saccharides in which several fructose molecules (e.g. 1 to 4 molecules) are bound to the galactose moiety of lactose through β1, 4 or β1, 6linkage, andmixtures thereof. Xylo-oligosaccharides as used herein refer to saccharides in which xylose molecules are jointed through β1, 4 linkage.

The expression "indigestible sugar alcohols" as used herein refers to sugar alcohols that are not at all or hardly digestible by digestive enzymes in the body.

The term "sugar alcohols" as used herein refers to polyhydric alcohols obtained by reducing carbonyl groups of sugars.

Examples of indigestible sugar alcohols include maltitol, erythritol, and xylitol.

In the present invention, indigestible oligosaccharides or indigestible sugar alcohols may be used singly or in combination with two or more indigestible oligosaccharides or indigestible sugar alcohols. Furthermore, one or more indigestible oligosaccharides may be used together with one or more indigestible sugar alcohols.

The term "mineral" as used herein refers to a nutrient selected from the group consisting of calcium, iron, magnesium, phosphorus and combinations thereof.

Calcium can be calcium carbonate, calcium phosphate, calcium chloride, calcium lactate, calcium gluconate, or calcium citrate.

Iron can be ferric citrate, iron phosphates (e.g., iron pyrophosphate), iron chlorides, or iron sulfates.

Magnesium can be magnesium oxide, magnesium carbonate, magnesium chloride, or magnesium sulfate.

Phosphorus can be sodium phosphate (primary or secondary) or potassium phosphate (primary or secondary).

Calcium, iron, magnesium, and phosphorus can be mixed into the mineral supply composition in a raw chemical form, a salt form, or an ion form. The salt form is preferable.

Natural products (e.g., bovine bones, heme iron, seaweed, and eggshells) rich in calcium, iron, magnesium, and phosphorus can also be formulated as minerals into the composition for mineral supply. For example, bovine bones can be formulated mainly for calcium, phosphate, and magnesium, heme iron mainly for iron, seaweed mainly for calcium and magnesium, and eggshells mainly for calcium.

The mineral supply composition according to the present invention used for the treatment of postgastrectomic syndrome contains at least calcium and iron as minerals, preferably, calcium, iron, magnesium and/or phosphorus.

The term "postgastrectomic syndrome" as used herein refers to bone metabolic disorders (e.g., dysostosis) and anemia (e.g., iron deficiency anemia).

The mineral supply composition according to the present invention used for supplying calcium or for treating abnormal bone metabolism contains at least calcium as a mineral, preferably, calcium, magnesium and/or phosphorus.

The mineral supply composition according to the present invention used for supplying iron or for treating anemia contains at least iron as a mineral, preferably, iron and calcium.

The ratio of calcium and indigestible oligosaccharides and/or indigestible sugar alcohols in the composition according to the present invention is preferably 1:1 to 1:40 (by weight), more preferably, 1:3 to 1:20.

The ratio of iron and indigestible oligosaccharides and/or indigestible sugar alcohols in the composition according to the present invention is preferably 1:500 to 1:5000 (by weight), more preferably, 1:750 to 1:2500.

The present invention also provide a method for the treatment of postgastrectomic syndrome, which comprises the administration of a mineral selected from the group consisting of calcium, iron, magnesium, phosphorus and combinations thereof together with indigestible oligosaccharides and/or indigestible sugar alcohols to a patient who underwent gastrectomy. Reference to the term "treatment" extends to "prophylaxis".

The composition according to the present invention may take the form of, for example, granules, capsules, tablets, powders, or liquids. The composition according to the present invention may be administered directly or in the form of a mixture with ordinary food products and drinks. Alternatively, the composition according to the present invention to be administered may contain seasonings, food additives, or the like. Diet forms are not particularly limited as long as the composition according to the present invention can be mixed with the diets. Pharmaceutically active ingredients can also be formulated into the composition according to the present invention.

A daily dose of the composition according to the present invention can be determined depending on the pathological state or the stage after the operation. Generally, indigestible oligosaccharides or indigestible alcohols can be administered to a patient who underwent gastrectomy in a liquid diet form preferably in a dosage of about 20 to 200 mg/kg of body weight. After returning to a normal diet, a dosage can be about 50 to 500 mg/kg of body weight.

EXAMPLES

The present invention is further illustrated by the following Examples that are not intended as a limitation of the invention.

Example 1

Twenty-eight SD male rats (5 week-old) (CLEA Japan, Inc.) were fed solid feed (MF) for one week prior to experiments. Rats were divided into two groups based on body weight at the end of the one-week feeding and subjected to either gastrectomy or pseudo operation. The pseudo operation herein means an operation in which the abdomen of the animal is opened by celiotomy to expose the stomach for the same period of time as spent for gastrectomy, and then sutured.

The animals were fed a recovery diet (control diet) for 8 days after the operation and divided on day 8 into the following 4 groups of 7 animals each based on body weight, i.e., 2 groups each for animals with gastrectomy and animals with pseudo operation:

(1) A group of animals which underwent pseudo operation and were fed a test diet without Supplemented Diet A according to the present invention (control diet) ("pseudo operation" group),
(2) A group of animals which underwent pseudo operation and were fed a test diet containing Supplemented Diet A according to the present invention (Supplemented Diet A) ("pseudo operation+supplemented diet" group),
(3) A group of animals which underwent gastrectomy and were fed a test diet without Supplemented Diet A according to the present invention (control diet) ("gastrectomy" group), and
(4) A group of animals which underwent gastrectomy and were fed a test diet containing Supplemented Diet A according to the present invention (Supplemented Diet A) ("gastrectomy+supplemented diet" group).

Test diets were given daily in the amount of 15 g per animal for 29 days. The compositions of the test diets are shown in Table 1. The animals were kept in a rearing room at 22±2° C. with a 12-hour cycle of light and darkness (8:00 to 20:00). The animals were allowed to take drinking water (pure water) anytime.

TABLE 1

Compositions of the test diets

|  | Control diet | Supplemented Diet A |
|---|---|---|
| Dextrin | 43.20 | 43.20 |
| Casein | 20.00 | 20.00 |
| Sucrose | 20.00 | 12.50 |
| Corn oil | 7.00 | 7.00 |
| Cellulose | 5.00 | 5.00 |
| Ca, Fe, Mg, P Free Mineral Mix | 1.46 | 1.46 |
| Vitamin Mix | 1.00 | 1.00 |
| L-Cystine | 0.30 | 0.30 |
| FOS | 0.00 | 7.50 |
| Calcium carbonate | 1.25 | 1.25 |
| Ferric citrate | 0.02 | 0.02 |
| Magnesium oxide | 0.08 | 0.08 |
| Potassium dihydrogenphosphate | 0.69 | 0.69 |

Ca, Fe, Mg, P Free Mineral Mix: AIN-93 (Oriental Yeast Co., Ltd.) from which Ca, Fe, Mg, and P were removed.

Vitamin Mix: AIN-93 Vitamin Mix (Oriental Yeast Co., Ltd.)

FOS: Meioligo P (Meiji Seika kaisha, Ltd.) (fructo-oligosaccharide purity: more than 95%)

Fecal samples were taken for consecutive 5 days starting 4, 11, 18 and 25 days after the start of feeding test diets (each referred to as the first week, the second week, the third week, and the fourth week). Animals were sacrificed at the end of the test, and samples of the blood, serum and right femur were taken. Calcium in ashed feeds, feces and femurs was measured using an ion plasma emission analyzer (ICPS-5000, Shimadzu Corp.) to calculate the content, concentration and absorption rate of calcium. Blood samples were taken into hematocrit tubes to measure hematocrit values. Serum iron concentrations were measured using the Fe Test Wako (Wako Pure Chemical Industries Ltd.).

Figure 1:
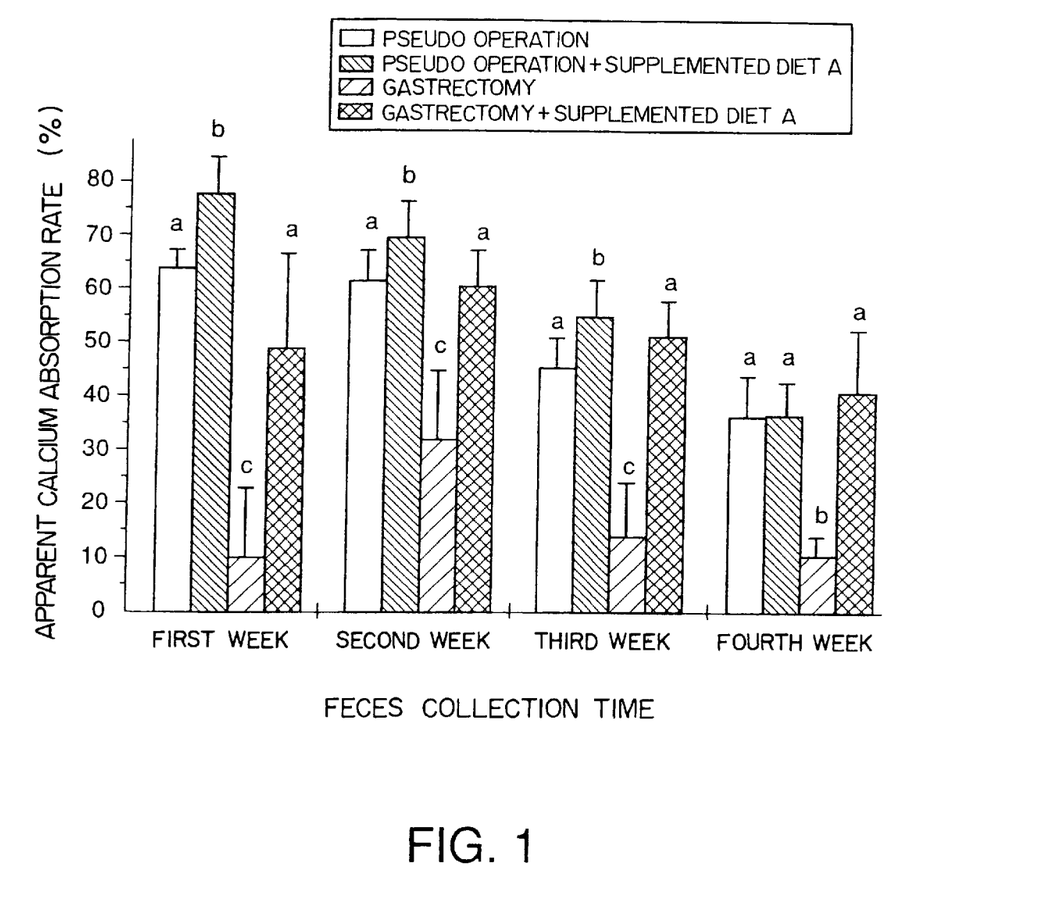
FIG. 1 shows changes in apparent calcium absorption rate in experimental rats (Example 1). A significant difference ($p<0.05$) exists among the groups as represented by the different appended letters (a, b and c).

FIG. 1 shows changes in apparent calcium absorption rates. The calcium absorption rates for "gastrectomy +supplemented diet" group were higher than "gastrectomy" group and increased up to those obtained for "pseudo operation" group and "pseudo operation+supplemented diet" group.

The apparent calcium absorption rate was calculated according to the following formula:

$$\text{Apparent calcium absorption (\%)} = \frac{\text{Calcium intake} - \text{Calcium excretion in feces}}{\text{Calcium intake}} \times 100$$

Figure 2:
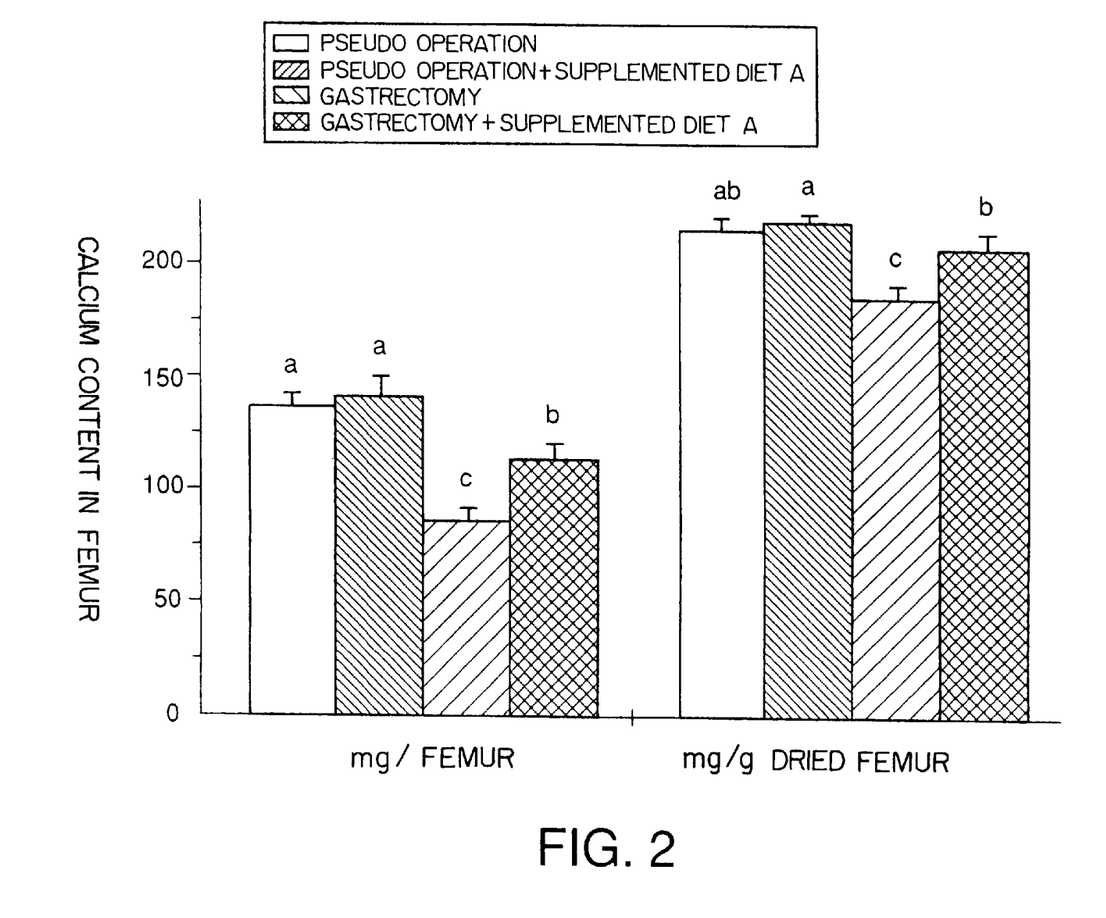
FIG. 2 shows calcium contents in the femurs of experimental rats (Example 1). A significant difference ($p<0.05$) exists among the groups as represented by the different appended letters (a, b and c).

FIG. 2 shows calcium content and concentration in the femurs. The values for "gastrectomy+supplemented diet" group were higher than "gastrectomy" group and increased almost up to those for "pseudo operation" group.

Figure 3:
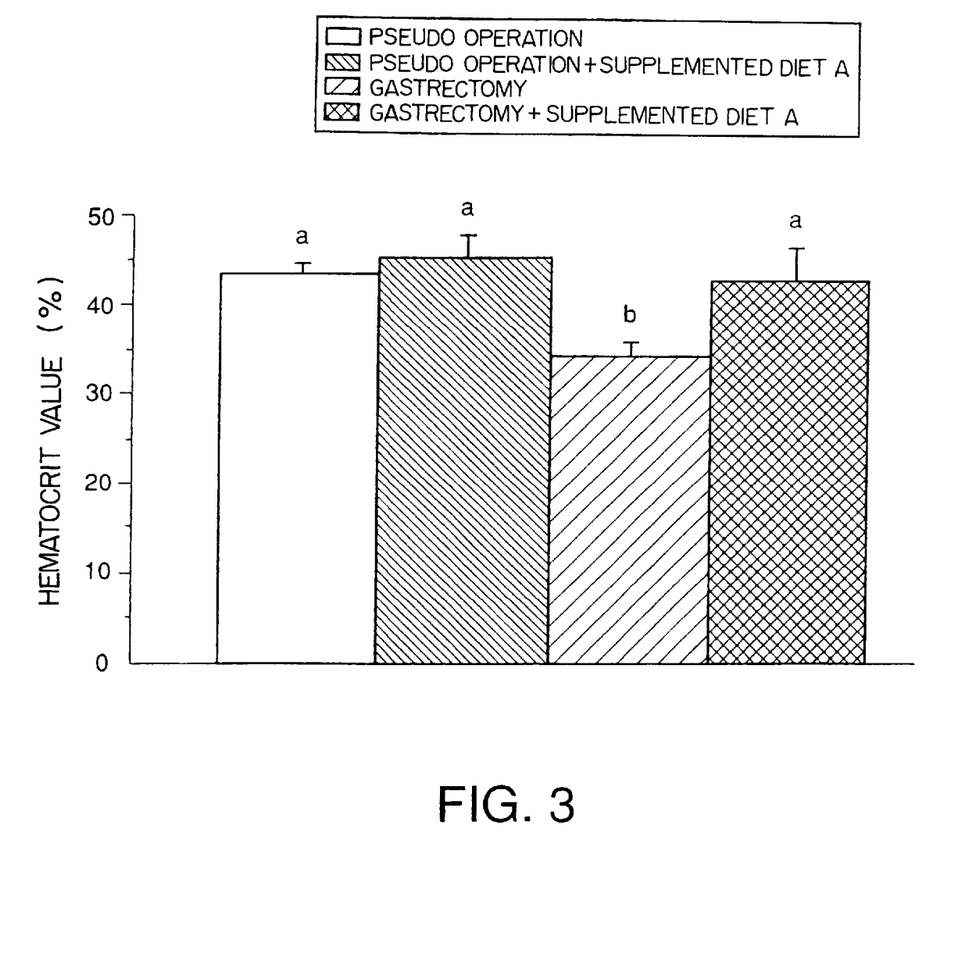
FIG. 3 shows hematocrit values in experimental rats (Example 1). A significant difference ($p<0.05$) exists among the groups as represented by the different appended letters (a, b and c).

FIG. 3 shows hematocrit values. The values for "gastrectomy+supplemented diet" group were higher than "gastrectomy" group and increased up to those for "pseudo operation" group and "pseudo operation+supplemented diet" group.

Figure 4:
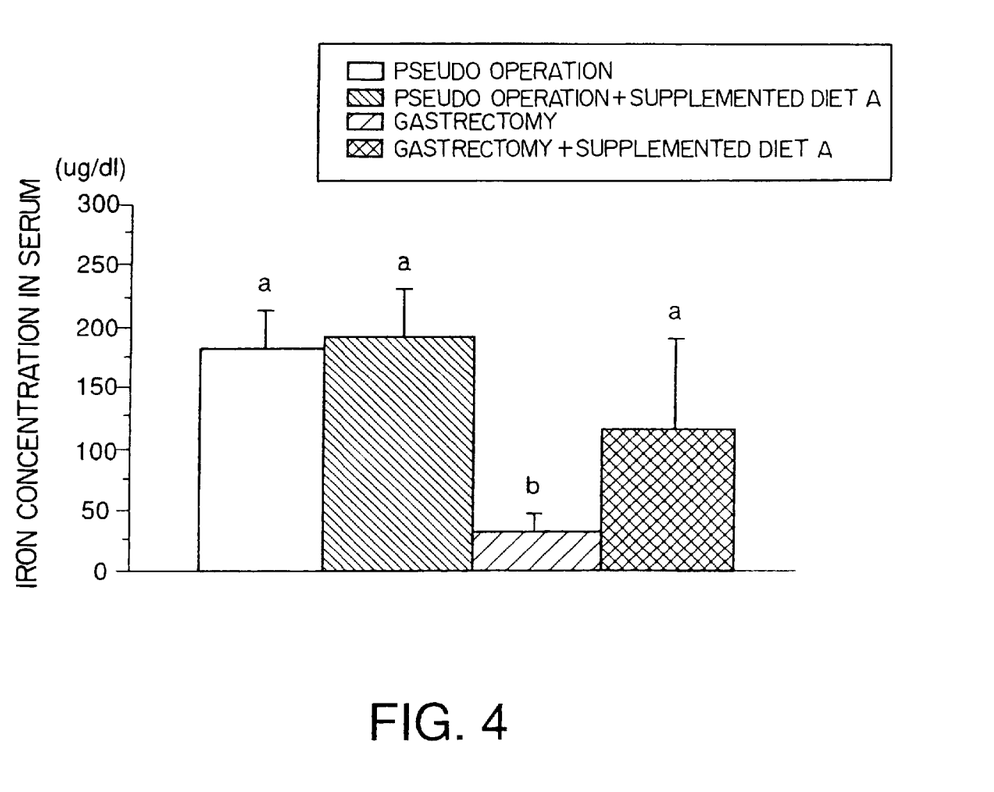
FIG. 4 shows iron contents in the serum of experimental rats (Example 1). A significant difference ($p<0.05$) exists among the groups as represented by the different appended letters (a, b and c).

FIG. 4 shows serum iron concentrations. The values for "gastrectomy+supplemented diet" group were higher than "gastrectomy" group and increased up to those for "pseudo operation" group and "pseudo operation+supplemented diet" group.

The results show that the ingestion of the supplemented diets according to the present invention increased calcium and iron absorption rates in "gastrectomy+supplemented diet" group and that postgastrectomic syndrome such as dysostosis and anemia was entirely prevented.

Example 2

Gastrectomy was carried out in the same manner as described in Example 1. On day 8 after the operation, animals were divided into the following 6 groups of 5 animals each based on the body weight:

(1) A group of animals fed a test diet without the supplemented diet according to the present invention (control diet) (control group),
(2) A group of animals fed a test diet containing Supplemented Diet A according to the present invention (Supplemented Diet A) ("Supplemented Diet A" group),
(3) A group of animals fed a test diet containing Supplemented Diet B according to the present invention (Supplemented Diet B) ("Supplemented Diet B" group),
(4) A group of animals fed a test diet containing Supplemented Diet C according to the present invention (Supplemented Diet C) ("Supplemented Diet C" group),
(5) A group of animals fed a test diet containing Supplemented Diet D according to the present invention (Supplemented Diet D) ("Supplemented Diet D" group), and
(6) A group of animals fed a test diet containing Supplemented Diet E according to the present invention (Supplemented Diet E) ("Supplemented Diet E" group).

The compositions of the test diets were shown in Table 2:

TABLE 2

Compositions of the test diets

| (%) | Control diet | Supplemented diets according to the present invention | | | | |
|---|---|---|---|---|---|---|
|  |  | A | B | C | D | E |
| Dextrin | 43.20 | 43.20 | 43.20 | 43.20 | 43.20 | 43.20 |
| Casein | 20.00 | 20.00 | 20.00 | 20.00 | 20.00 | 20.00 |
| Sucrose | 20.00 | 12.50 | 10.00 | 12.50 | 5.00 | 5.00 |
| Corn oil | 7.00 | 7.00 | 7.00 | 7.00 | 7.00 | 7.00 |
| Cellulose | 5.00 | 5.00 | 5.00 | 5.00 | 5.00 | 5.00 |

TABLE 2-continued

Compositions of the test diets

| (%) | Control diet | Supplemented diets according to the present invention | | | | |
| --- | --- | --- | --- | --- | --- | --- |
| | | A | B | C | D | E |
| Ca, Fe, Mg, P Free Mineral Mix | 1.46 | 1.46 | 1.46 | 1.46 | 1.46 | 1.46 |
| Vitamin Mix | 1.00 | 1.00 | 1.00 | 1.00 | 1.00 | 1.00 |
| L-Cystine | 0.30 | 0.30 | 0.30 | 0.30 | 0.30 | 0.30 |
| FOS | 0.00 | 7.50 | 0.00 | 0.00 | 0.00 | 0.00 |
| Galacto-oligosaccharide | 0.00 | 0.00 | 10.00 | 0.00 | 0.00 | 0.00 |
| Raffinose | 0.00 | 0.00 | 0.00 | 7.50 | 0.00 | 0.00 |
| Maltitol | 0.00 | 0.00 | 0.00 | 0.00 | 15.00 | 0.00 |
| Lactosucrose | 0.00 | 0.00 | 0.00 | 0.00 | 0.00 | 15.00 |
| Calcium carbonate | 1.25 | 1.25 | 1.25 | 1.25 | 1.25 | 1.25 |
| Ferric citrate | 0.02 | 0.02 | 0.02 | 0.02 | 0.02 | 0.02 |
| Magnesium oxide | 0.08 | 0.08 | 0.08 | 0.08 | 0.08 | 0.08 |
| Potassium dihydrogen-phosphate | 0.69 | 0.69 | 0.69 | 0.69 | 0.69 | 0.69 |

Ca, Fe, Mg, P Free Mineral Mix: AIN-93 from which Ca, Fe, Mg, and P were removed.

Vitamin Mix: AIN-93 Vitamin Mix.

FOS: Meioligo P (fructo-oligosaccharide purity: more than 95%).

Galacto-oligosaccharide: Cup Oligo (Yakult Honsha, Co., Ltd.) (galacto-oligosaccharide purity: more than 70%)

Raffinose: Beat Oligo (Nippon Beet Sugar MFG. Co., Ltd.) (oligosaccharide purity: more than 98%)

Maltitol: Mabit Oligo (Hayashibara Co., Ltd.) (maltitol purity: more than 88%)

Lactosucrose: Nyuka Oligo (Ensuiko Seito, Co., Ltd.) (lactosucrose purity: more than 55%)

Animals were reared under the same conditions as described in Example 1. After completion of the test, samples of right femurs were taken and hematocrit value and calcium content and concentration were measured.

Figure 5:
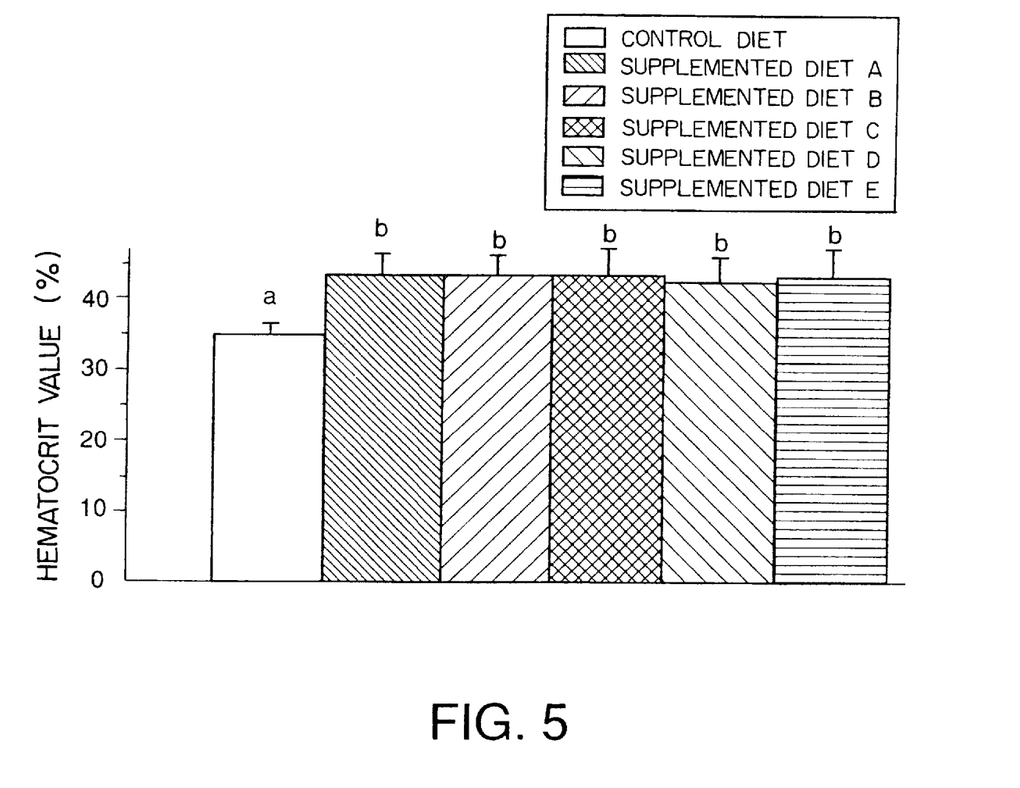
FIG. 5 shows hematocrit values in experimental rats (Example 2). A significant difference ($p<0.05$) exists among the groups as represented by the different appended letters (a, b and c).
Figure 6:
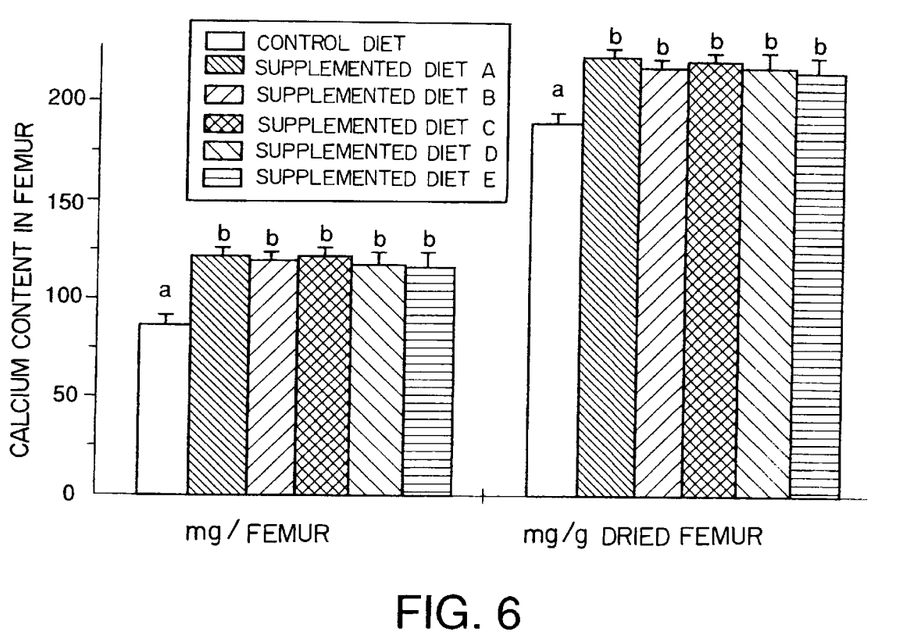
FIG. 6 shows calcium contents in the femurs of experimental rats (Example 2). A significant difference ($p<0.05$) exists among the groups as represented by the different appended letters (a, b and c).

As shown in FIG. 5, hematocrit values for the groups fed the supplemented diets according to the present invention were higher than the control group. As shown in FIG. 6, calcium contents and concentrations in the femurs for the groups fed the supplemented diets according to the present invention were higher than the control group.

The results show that the ingestion of the supplemented diets according to the present invention increased the calcium and iron absorption rates in the group fed the supplemented diets according to the present invention and that postgastrectomic syndrome such as dysostosis and anemia was entirely prevented.

What is claimed is:

1. A method for treating postgastrectomic syndrome comprising administering a mineral together with an indigestible oligosaccharide and/or an indigestible sugar alcohol to a patient who underwent gastrectomy.

2. The method according to claim 1, wherein the indigestible oligosaccharide is selected from the group consisting of fructo-oligosaccharides, raffinose, galacto-oligosaccharides, and lactosucrose.

3. The method according to claim 1, wherein the indigestible sugar alcohol is maltitol.

4. The method according to claim 1, wherein the mineral is selected from the group consisting of calcium, iron, magnesium, phosphorus, and combinations thereof.

5. The method according to claim 1, wherein the mineral is calcium and/or iron.

6. The method according to claim 1, wherein the postgastrectomic syndrome is bone metabolic disorders.

7. The method according to claim 1, wherein the post gastrectomic syndrome is anemia.

8. A method for supplying postgastrectomic mineral comprising administering a mineral together with an indigestible oligosaccharide and/or an indigestible sugar alcohol to a patient who underwent gastrectomy.

9. The method according to claim 8, wherein the indigestible oligosaccharide is selected from the group consisting of fructo-oligosaccharides, raffinose, galacto-oligosaccharides, and lactosucrose.

10. The method according to claim 8, wherein the indigestible sugar alcohol is maltitol.

11. The method according to claim 8, wherein the mineral is selected from the group consisting of calcium, iron, magnesium, phosphorus, and combinations thereof.

12. The method according to claim 8, wherein the mineral is calcium and/or iron.

13. The method according to claim 8, which supplies calcium to the patient.

14. The method according to claim 8, which supplies iron to the patient.

\* \* \* \* \*